United States Patent [19]
Pellico

[11] Patent Number: 5,718,886
[45] Date of Patent: *Feb. 17, 1998

[54] STABILIZED ANHYDROUS TOOTH WHITENING GEL

[75] Inventor: Michael A. Pellico, Los Angeles, Calif.

[73] Assignee: Laclede Professional Products, Inc., Gardena, Calif.

[*] Notice: The term of this patent shall not extend beyond the expiration date of Pat. No. 5,631,000.

[21] Appl. No.: 772,422

[22] Filed: Dec. 23, 1996

Related U.S. Application Data

[63] Continuation-in-part of Ser. No. 599,364, Mar. 11, 1996, Pat. No. 5,631,000.

[51] Int. Cl.$^6$ ............... A61K 7/16; A61C 5/00
[52] U.S. Cl. ........................ 424/53; 433/215
[58] Field of Search ........................ 424/53

[56] References Cited

U.S. PATENT DOCUMENTS

| | | | |
|---|---|---|---|
| 5,098,303 | 3/1992 | Fischer | 433/215 |
| 5,234,342 | 8/1993 | Fischer | 433/215 |
| 5,290,566 | 3/1994 | Schow | 424/488 |
| 5,376,006 | 12/1994 | Fischer | 424/53 |
| 5,409,631 | 4/1995 | Fischer | 424/53 |
| 5,425,953 | 6/1995 | Sintov et al. | 424/53 |
| 5,631,000 | 5/1997 | Pellico et al. | 424/53 |

*Primary Examiner*—Peter F. Kulkosky
*Attorney, Agent, or Firm*—Donald Diamond

[57] ABSTRACT

Stabilized anhydrous dental whitening gel compositions are provided which resist viscosity degradation during oral use. An illustrative anhydrous dental bleaching gel composition embodying this feature comprises propylene glycol, polyethylene glycol, glycerin in an amount not exceeding about 10 wt. %, neutralized carboxypolymethylene, hydroxypropylcellulose, xanthan gum and carbamide peroxide.

18 Claims, No Drawings

5,718,886

STABILIZED ANHYDROUS TOOTH WHITENING GEL

CROSS-REFERENCE TO RELATED APPLICATION

This application is a continuation-in-part of U.S. patent application Ser. No. 08/599,364 filed Mar. 11, 1996 now U.S. Pat. No. 5,631,000 and entitled Anhydrous Tooth Whitening Gel.

FIELD OF THE INVENTION

This invention relates to dental compositions and, more particularly, to stabilized anhydrous tooth whitening gel compositions, a method for preparing the gel compositions, and a method for utilizing the gel compositions.

PRIOR ART

In that aspect of aesthetic dentistry which relates to self-administered use of in-home tooth whitening compositions, the dental patient is provided with a custom-fitted dental tray having selectively enlarged tooth treating compartments which are adapted to receive a whitening gel that is dispensed from a syringe. The dental tray, with its gel content, is unobtrusively and advantageously worn by the patient at night and while the patient sleeps. This treatment is repeated for a sufficient period of time to effect the tooth bleaching and whitening process.

It is disclosed in the prior art that carboxypolymethylene as well as methylcelluose can be used as the gelation agents in the formulation of tooth whitening gels. The prior art also discloses that carbamide peroxide (urea peroxide) as well as hydrogen peroxide can be used as the whitening agents in the formulation of tooth whitening gels.

U.S. Pat. No. 5,290,566 (Schow, et al., 1994) discloses a tooth whitening gel containing urea peroxide (carbamide peroxide), methylcelluose and water wherein the concentration of urea peroxide is from about 22 to about 32 wt. %.

U.S. Pat. Nos. 5,098,303 (Fischer, 1992), 5,234,342 (Fischer, 1993), 5,376,006 (Fischer, 1994) and 5,409,631 (Fischer, 1995), which are incorporated herein by reference, disclose tooth bleaching and whitening gel compositions formulated with carbamide peroxide, water, glycerin, carboxypolymethylene and sodium hydroxide. With respect to broad range ingredient concentration, the formulations contain from about 3.0 to about 20 wt. % carbamide peroxide, from about 10 to about 60 wt. % water, from about 20 to about 70 wt. % glycerin, from about 3.5 to about 12 wt. % carboxypolymethylene and sodium hydroxide in an amount to substantially neutralize the carboxypolymethylene. The gel is characterized as comprising a saturated or super saturated carboxypolymethylene composition wherein the actual concentration of carboxypolymethylene in the total quantity of water in the gel composition is in the range from about 15% to about 40%, with the concentrated carboxypolymethylene providing the gel composition with a tackiness or stickiness. As to gel preparation, the patentee recommends that the carboxypolymethylene be mixed with glycerin and the resulting admixture dispersed in water, followed by the addition of the remaining ingredients, namely, sodium hydroxide and carbamide peroxide.

It has been observed that carbamide peroxide tooth whitening gels containing relatively high concentrations of water, glycerin and carboxypolymethylene (a) tend to have limited package stability as a result of the interaction of carbamide peroxide with water, (b) tend to increase tooth sensitivity as a result of the hygroscopic properties of glycerin which can reduce the moisture level at the tooth treatment surface, and (c) tend to string from one tooth treating compartment in the bleaching tray to the next tooth treating compartment in the tray in the course of syringe loading the compartments with the bleaching gel.

Although the foregoing limitations have been addressed by the development and use of anhydrous tooth whitening gels, it has now been observed that tooth whitening gels formulated with thickeners such as carboxypolymethylene and/or cellulosics exemplified by carboxymethylcullulose, hydroxymethylcellulose and hydroxypropylcellulose tend to decrease in viscosity with an increase in temperature. During overnight oral application of the tooth whitening gel, the temperature of the gel in the dental tray can increase from ambient to about 37° C. (98.6° F.). As a result of this rise in temperature, the gel tends to thin and become somewhat flowable. If the gel gets too thin, it may flow out of the tray and into contact with the soft tissue, causing tissue irritation.

SUMMARY OF THE INVENTION

An important object of the present invention is to provide new and improved dental whitening compositions which address the viscosity limitations of the prior art tooth whitening gels as hereinabove described.

Another object of this invention is to provide tooth whitening gel compositions which enable a reduced concentration of carboxypypolmythylene to be used as a thickener without impairing the requisite viscosity characteristics of the gel compositions during oral use.

A further object of this invention is to provide tooth whitening gel compositions which resist viscosity degradation during oral use.

An additional object of this invention is to provide tooth whitening gel compositions which retain their viscosity in the presence of an increase in temperature and a decrease in pH that are encountered during oral use.

These and other objects and features of the present invention are accomplished with the compositions, methods and procedures as described herein.

In accordance with one aspect of this invention, there is provided a tooth whitening composition containing carbamide peroxide dispersed in a substantially anhydrous gelatinous carrier. The anhydrous carrier comprises a polyol component wherein glycerin, if present, is limited to an amount that does not exceed about 10 wt. % based on the total weight of the composition. The anhydrous carrier also comprises a thickener component containing neutralized carboxypolymethylene, cellulosic ether soluble in the polyol component and a viscosity stabilizer comprising xanthan gum.

In accordance with a second aspect of this invention, there is provided a method for whitening teeth which comprises (1) extruding a substantially anhydrous tooth whitening gel composition into the reservoir system of a dental bleaching tray, (2) placing the dental tray in the oral cavity so as to bring the gel composition into contact with the teeth to be whitened, (3) maintaining the gel composition in contact with the aforesaid teeth for a plurality of hours per day, and (4) repeating steps 1, 2 and 3 for multiple days to effect whitening of the teeth. The anhydrous tooth whitening gel composition which can be used in carrying out the method advantageously comprises (a) propylene glycol in an amount from about 10 wt. % to about 50 wt. %, (b) polyethylene glycol in an amount from about 10 wt. % to about 55 wt. %, and having a molecular weight from about 400 to about 1500, (c) glycerin in an amount from about 0 wt. % to about 10 wt. %, (d) carboxypolymethylene in an amount from about 0.5 wt. % to about 3.0 wt. %, (e) hydroxypropylcellulose in an amount from about 0.5 wt. % to about 10 wt. %, (f) xanthan gum in an amount from about 0.1 wt % to about 1.5 wt. %, (g) neutralizing reagent in an amount to substantially neutralize carboxypolymethylene, and (g) carbamide peroxide in an amount from about 5.0 wt. % to about 25 wt. %.

In accordance with a third aspect of this invention, there is provided a method for preparing substantially anhydrous dental whitening gel compositions. The method comprises admixing a settable ingredient mix to obtain a homogenous dispersion of the ingredients. The settable ingredient mix advantageously comprises (a) propylene glycol in an amount from about 10 wt. % to about 55 wt. %, (b) polyethylene glycol in an amount from about 10 wt. % to about 50 wt. %, and having a molecular weight from about 400 to about 1500, (c) glycerin in an amount from about 0 wt. % to about 10 wt. %, (d) carboxypolymethylene in an amount from about 0.5 wt. % to about 3.0 wt. %, (e) hydroxypropylcellulose in an amount from about 0.5 wt. % to about 10 wt. %, (f) xanthan gum in an amount from about 0.1 wt % to about 1.5 wt. %, (g) neutralizing reagent in an amount to substantially neutralize carboxypolymethylene, and (h) carbamide peroxide in an amount from about 5.0 wt. % to about 25 wt. %, (i) wherein weight percent is based on the total weight of the gel composition.

DETAILED DESCRIPTION

The dental whitening gel compositions of this invention comprise carbamide peroxide dispersed in an anhydrous gelatinous carrier. Carbamide peroxide is generally present in the anhydrous gel compositions in an amount from about 5 wt. % to about 25 wt. % and, preferably, in an amount from about 10 wt. % to about 20 wt. %.

The anhydrous gelatinous carrier comprises a liquid component and a thickener component. Liquid polyols such as propylene glycol and polyethylene glycol are advantageously used in formulating the liquid component. Propylene glycol is generally present in the gel compositions in an amount from about 10 wt. % to about 55 wt. % and, preferably, in an amount from about 25 wt. % to about 45 wt. %. Polyethylene glycol which can be used in the practice of this invention has a molecular weight from about 400 to about 1500 and is generally present in the gel compositions in an amount from about 10 wt. % to about 50 wt. % and, preferably, in an amount from about 25 wt. % to about 45 wt. %.

Glycerin can also be used as a constituent of the liquid component. However, glycerin is hygroscopic and a high concentration of glycerine in the gel tends to pull moisture away from the surface of the teeth which can lead to increased dental sensitivity to the bleaching composition. Accordingly, if glycerin is used in the bleaching gel, it should be limited to a concentration that does not exceed about 10 wt. % of the gel composition. In a more specific aspect, glycerin can be present in the gel composition in an amount from about 3.0 wt. % to about 9.0 wt. %.

The thickener portion of the gel composition advantageously contains a blend of neutralized carboxypolymethylene and cellulosic ether that is soluble in the liquid component. Carboxypolymethylene is generally present in the gel compositions in an amount from about 0.5 wt. % to about 3.0 wt. % and, preferably, in an amount from about 1.5 wt. % to about 2.5 wt. %. Carboxypolymethylene is characterized as a slightly acidic vinyl polymer with active carboxyl groups. Typically, the acidic carboxypolymethylene is neutralized in situ during the preparation of the gel composition by adding an anhydrous alkalinizing agent such as anhydrous sodium hydroxide to the pre-gelatinous mix in order to bring the pH of the gel composition to an orally acceptable level as, for example, a pH from about 6.0 to about 7.5.

Cellulosic ether is generally present in the gel compositions in an amount from about 0.5 wt. % to about 10 wt. % and, preferably, in an amount from about 1.0 wt. % to about 3.0 wt. %. A preferred cellulosic ether is hydroxypropylcellulose.

The blend of neutralized carboxypolymethylene and cellulosic ether is particularly advantageous because the blend provides the gel compositions with improved thixotropic properties in respect of flow-set characteristics. This rheological enhancement constitutes an improvement in the dental whitening art because it tends to minimize the stringing and roping of the gel from one tooth treating compartment to the next tooth treating compartment during the sequential syringe loading of the gel into the compartments of the dental whitening tray.

Xanthan gum is generally present in the gel compositions in an amount from about 0.1 wt. % to about 1.5 wt. % and, preferably, in an amount from about 0.3 wt. % to about 1.3 wt. %. Xanthan gum, (Merck Index No. 10191, 12th ed.), is available under the trademark Keltrol. Xanthan gum is prescribed as an exocellular heteropolysaccharide produced via a closely controlled fermentation of the bacteria Xanthamonas campestries and its structure is characterized as a cellulose backbone with trisaccharide side claims in alternating anhydroglucose units consisting of a glucuronic acid residue between two mannose units wherein the molecule exists as a right-handed, fivefold helix with the trisaccharide side claims effectively shielding the backbone.

The anhydrous tooth whitening gels of this invention are prepared by adding and mixing the ingredients of the formulation in a suitable vessel such as a stainless steel tank that is provided with a heavy duty mixer which is suitable for use with thick gels. If desired, the mixing vessel can be combined with vacuum equipment for carrying out the admixing of the ingredients under vacuum conditions. The ingredients of the formulation are mixed to obtain a homogenous dispersion which sets to a thixotropic gel.

In the preparation of the dental whitening gels, the formulating ingredients are advantageously added to the mixing vessel in the following order: liquid ingredients, thickener ingredients, alkalinizing agent, carbamide peroxide, and any desired flavoring.

The quantities of the formulating ingredients are so selected as to provide the whitening gels with a composition containing (a) propylene glycol in an amount from about 10 wt. % to about 55 wt. % and, preferably, in an amount from about 25 wt % to about 45 wt. %, (b) polyethylene glycol in an amount from about 10 wt. % to about 50 wt. % and, preferably, in am amount from about 25 wt. % to about 45 wt. % and having a molecular weight from about 400 to about 1500, (c) glycerin in an amount from about 0 wt. % to about 10 wt. % and, preferably, in an amount from about 3.0 wt. % to about 9.0 wt. %, (d) carboxypolymethylene in an amount from about 0.5 wt. % to about 3.0 wt. % and, preferably, in an amount from about 1.5 wt. % to about 2.5 wt. %, (e) hydroxypropylcellulose in an amount from about 0.5 wt. % to about 10 wt. % and, preferably, in an amount from about 1.0 wt. % to about 3.0 wt. % (f) xanthan gum in an amount from about 0.1 wt. % to about 1.5 wt. % and, preferably, in an amount from about 0.3 wt. % to about 1.3 wt. %, (g) neutralizing reagent, preferably, anhydrous sodium hydroxide in an amount to substantially neutralize carboxypolymethylene, and (h) carbamide peroxide in an amount from about 5.0 wt. % to about 25 wt. % and, preferably, in an amount from about 10 wt. % to about 20 wt. %.

EXAMPLES

The following examples further illustrate the anhydrous tooth whitening gels of this invention and the concentration ranges for the ingredients thereof. As used in the examples, "PEG" is a trade designation for polyethylene glycol (Merck Index No. 7545, 11th ed.), "Carbopol" is a trademark for carboxypolymethylene (Merck Index No. 1836, 11th ed.) and "Klucel" is a trademark for hydroxypropylcellulose (Merck Index No. 4776, 11th ed.). The bleaching gels were prepared in accordance with the method and procedure as hereinabove described.

| Ingredients | Weight Percent | | | | |
|---|---|---|---|---|---|
| | Ex. 1 | Ex. 2 | Ex. 3 | Ex. 4 | Ex. 5 |
| Propylene glycol | 47.4 | 49.0 | 45.4 | 43.4 | 48.4 |
| PEG 600 | 20.0 | 21.7 | — | 16.0 | 15.0 |
| PEG 1000 | 10.0 | 11.7 | — | — | 15.0 |
| PEG 1450 | — | — | 26.0 | 6.0 | — |
| PEG 1500 | — | — | — | — | — |
| Glycerin | 8.0 | 8.0 | 8.0 | 8.0 | 7.0 |
| Carbopol 980 | 2.2 | 2.2 | 2.2 | 2.2 | 2.2 |
| Klucel GFF | 1.7 | 1.5 | 1.0 | 0.8 | 1.3 |
| Xanthan gum | 0.1 | 0.3 | 0.8 | 1.0 | 1.3 |
| Flavor | 0.2 | 0.2 | 0.2 | 0.2 | 0.2 |
| Sodium hydroxide | 0.4 | 0.4 | 0.4 | 0.4 | 0.4 |
| Carbamide peroxide | 10.0 | 5.0 | 16.0 | 22.0 | 10.0 |
| | 100.0 | 100.0 | 100.0 | 100.0 | 100.0 |

| Ingredients | Weight Percent | | | |
|---|---|---|---|---|
| | Ex. 6 | Ex. 7 | Ex. 8 | Ex. 9 |
| Propylene glycol | 46.4 | 45.4 | 54.2 | 41.1 |
| PEG 600 | — | — | 28.0 | — |
| PEG 1000 | 31.0 | 16.0 | — | — |
| PEG 1450 | — | 16.0 | — | — |
| PEG 1500 | — | — | — | 35.2 |
| Glycerin | 8.0 | 8.0 | 3.0 | 3.0 |
| Carbopol 980 | 2.1 | 2.0 | 0.5 | 2.0 |
| Xanthan gum | 0.1 | 0.2 | 1.5 | 1.0 |
| Klucel GFF | 1.8 | 1.8 | 0.4 | 1.0 |
| Klucel MFF | — | — | 0.8 | — |
| Flavor | 0.2 | 0.2 | 0.2 | 0.2 |
| Sodium hydroxide | 0.4 | 0.4 | 0.4 | 0.5 |
| Carbamide peroxide | 10.0 | 10.0 | 11.0 | 16.0 |
| | 100.0 | 100.0 | 100.0 | 100.0 |

The anhydrous tooth whitening gel compositions, as hereinabove described, are packaged in appropriate syringes for dispensing into custom-fitted dental trays that are usually worn at night, but can also be worn during the day, with maximum whitening generally occurring when the treatment is continued for ten to fourteen days. The custom-fitted dental bleaching trays can be prepared by using materials and procedures that are well known in the dental art, and which are described in the prior art cited herein.

In a first alternative packaging embodiment, the dental whitening gels can be packaged in gel dispensing tubes or bottles for extrusion into general purpose dental trays for carrying out the dental whitening process. In a second alternative packaging embodiment, pre-packaged dental trays can be provided to the user containing dental whitening gels which have been adapted for this purpose.

In view of the foregoing descriptions and examples, it will become apparent to those of ordinary skill in the art that equivalent modifications thereof may be made without departing from the spirit and scope of this invention.

That which is claimed is:

1. A tooth whitening gel composition comprising carbamide peroxide dispersed in an anhydrous gelatinous carrier, said carrier comprising:
   (a) a polyol component wherein glycerin, if present, is limited to an amount that does not exceed about 10 wt. % based on the total weight of the composition;
   (b) a thickener component containing neutralized carboxypolymethylene and cellulosic either soluble in the polyol component; and
   (c) xanthan gum in an amount from about 0.1 wt. % to about 1.5 wt. % for stabilizing the gel composition against viscosity degradation during oral use.

2. The composition of claim 1 wherein the concentration of xanthan gum is from about 0.3 wt. % to about 1.3 wt. %.

3. The composition of claim 1 wherein the liquid polyol includes propylene glycol in an amount from about 10 wt. % to about 55 wt. % based on the total weight of the composition and polyethylene glycol in an amount from about 10 wt. % to about 50 wt. % based on the total weight of the composition, said polyethylene glycol having a molecular wt. from about 400 to about 1500.

4. The composition of claim 1 wherein glycerin is present in an amount from about 3.0 wt. % to about 9.0 wt. %.

5. The thickener of claim 1 wherein the cellulosic ether is hydroxypropylcelluose in an amount from about 0.5 wt. % to about 10 wt. % based on the total weight of the composition and the concentration of carboxypolymethylene in the composition is from about 0.5 wt. % to about 3.0 wt. %.

6. The composition of claim 1 wherein the concentration of carbamide peroxide is from about 5.0 wt. % to about 25 wt. %.

7. An anhydrous tooth whitening gel composition comprising:
   (a) propylene glycol in an amount from about 10 wt. % to about 55 wt. %,
   (b) polyethylene glycol in an amount from about 10 wt. % to about 50 wt. %, and having a molecular weight from about 400 to about 1500,
   (c) glycerin in an amount from about 0 wt. % to about 10 wt. %,
   (d) carboxypolymethylene in an amount from about 0.5 wt. % to about 3.0 wt. %,
   (e) hydroxypropylcellulose in an amount from about 0.5 wt. % to about 10 wt. %,
   (f) xanthan gum in an amount from about 0.1 wt. % to about 1.5 wt. %,
   (g) neutralizing reagent in an amount to substantially neutralize carboxypolymethylene, and
   (g) carbamide peroxide in an amount from about 5.0 wt. % to about 25 wt. %.

8. The composition of claim 7 wherein xanthan gum is present in amount from about 0.3 wt. % to about 1.3 wt. %.

9. The composition of claim 7 wherein propylene glycol is present in an amount from about 25 wt. % to about 45 wt. % and polyethylene glycol is present in an amount from about 25 wt. % to about 45 wt. %.

10. The composition of claim 7 wherein glycerin is present in an amount from about 3.0 wt. % to about 9.0 wt. %.

11. The composition of claim 7 wherein carboxypolymethylene is present in an amount from about 1.5 wt. % to about 2.5 wt. % and hydroxypropylcellulose is present in an amount from about 1.0 wt. % to about 3.0 wt. %.

12. The composition of claim 7 wherein carbamide peroxide is present in an amount from about 10 wt. % to about 20 wt. %.

13. A method for whitening teeth which comprises:
   (1) extruding an anhydrous teeth whitening gel composition into the reservoir system of a teeth bleaching dental tray, said gel composition comprising:
      (a) propylene glycol in an amount from about 10 wt. % to about 55 wt. %,
      (b) polyethylene glycol in an amount from about 10 wt. % to about 50 wt. %, and having a molecular weight from about 400 to about 1500,
      (c) glycerin in an amount from about 0 wt. % to about 10 wt. %,
      (d) carboxypolymethylene in an amount from about 0.5 wt. % to about 3.0 wt. %,
      (e) hydroxypropylcellulose in an amount from about 0.5 wt. % to about 10 wt. %,
      (f) xanthan gum in an amount from about 0.1 wt. % to about 1.5 wt. %,
      (g) neutralizing reagent in an amount to substantially neutralize carboxypolymethylene, and
      (h) carbamide peroxide in an amount from about 5.0 wt. % to about 25 wt. %;
   (2) placing said dental tray in the oral cavity so as to bring the gel composition into contact with the teeth to be whitened;
   (3) maintaining said gel composition in contact with said teeth for a plurality of hours per day; and
   (4) repeating steps 1, 2 and 3 for multiple days to thereby whiten the teeth.

14. The method of claim 13 wherein xanthan gum is present in an amount from about 0.3 wt. % to about 1.3 wt. %.

15. The method of claim 13 wherein glycerin is present in the gel composition in an amount from about 3.0 wt. % to about 9.0 wt. %; carboxypolymethylene is present in the gel composition in an amount from about 1.5 wt. % to about 2.5 wt. %; and hydroxypropylcellulose is present in the gel composition in an amount from about 1.0 wt. % to about 3.0 wt. %.

16. A method for preparing an anhydrous tooth whitening gel composition, which method comprises admixing:
   (a) propylene glycol in an amount from about 10 wt. % to about 55 wt. %,
   (b) polyethylene glycol in an amount from about 10 wt. % to about 50 wt. %,
   (c) glycerin in an amount from about 0 wt. % to about 10 wt. %,
   (d) carboxypolymethylene in an amount from about 0.5 wt. % to about 3.0 wt. %,
   (e) hydroxypropylcellulose in an amount from about 0.5 wt. % to about 10 wt. %,
   (f) xanthan gum in an amount from about 0.1 wt. % to about 1.5 wt. %,
   (g) neutralizing reagent in an amount to substantially neutralize carboxypolymethylene, and
   (h) carbamide peroxide in an amount from about 5.0 wt. % to about 25 wt. %,
   (i) wherein weight percent is based on the total weight of the gel composition.

17. The method of claim 16 wherein the amount of glycerin is from about 3.0 wt. % to about 9.0 wt. %, the amount of carboxypolymethylene is from about 1.5 wt. % to about 2.5 wt. %, the amount of hydroxypropylcellulose is from about 1.0 wt. % to about 3.0 wt. %, and the amount of xanthan gum is from about 0.3 wt. % to about 1.3 wt. %.

18. The method of claim 16 wherein said admixing is carried out under vacuum conditions.

* * * * *